United States Patent
Yamada et al.

(10) Patent No.: US 8,740,821 B2
(45) Date of Patent: Jun. 3, 2014

(54) MEDICAL APPARATUS

(75) Inventors: Norihiro Yamada, Hino (JP); Yukihiko Sawada, Yoshikawa (JP); Tamaki Watanabe, Irvine, CA (US)

(73) Assignee: Olympus Medical Systems Corp. (JP)

( * ) Notice: Subject to any disclaimer, the term of this patent is extended or adjusted under 35 U.S.C. 154(b) by 0 days.

(21) Appl. No.: 13/559,808

(22) Filed: Jul. 27, 2012

(65) Prior Publication Data

US 2013/0060169 A1 Mar. 7, 2013

Related U.S. Application Data

(63) Continuation of application No. PCT/JP2011/075731, filed on Nov. 8, 2011.

(60) Provisional application No. 61/412,143, filed on Nov. 10, 2010.

(51) Int. Cl.
*A61H 1/00* (2006.01)
*A61B 17/22* (2006.01)
*A61N 7/00* (2006.01)
*A61N 7/02* (2006.01)

(52) U.S. Cl.
CPC ............ *A61B 17/22012* (2013.01); *A61N 7/00* (2013.01); *A61N 7/02* (2013.01)
USPC .......................................................... 601/2

(58) Field of Classification Search
USPC .......................................................... 601/2
See application file for complete search history.

(56) References Cited

U.S. PATENT DOCUMENTS

| | | | |
|---|---|---|---|
| 4,922,902 A | 5/1990 | Wuchinich et al. | 604/22 |
| 6,997,883 B1 * | 2/2006 | Hahn | 600/560 |
| 2004/0092883 A1 * | 5/2004 | Casey et al. | 604/191 |
| 2005/0004469 A1 * | 1/2005 | Tsuzuki | 600/458 |
| 2006/0247662 A1 * | 11/2006 | Schwartz et al. | 606/114 |
| 2008/0044789 A1 * | 2/2008 | Johnson | 433/81 |
| 2008/0197218 A1 * | 8/2008 | Ishigaki et al. | 241/5 |

FOREIGN PATENT DOCUMENTS

| | | |
|---|---|---|
| JP | 9-509344 | 9/1997 |
| JP | 2002-058679 | 2/2002 |
| JP | 2003-010201 | 1/2003 |
| JP | 2009-261667 | 11/2009 |
| JP | 2010-522030 | 7/2010 |

OTHER PUBLICATIONS

English translation of Search Report issued by PCT Patent Office and received by applicant on May 23, 2013 in connection with corresponding EP patent application No. PCT/JP2011/075731.
International Search Report mailed Feb. 14, 2012 in corresponding PCT International Application No. PCT/JP2011/075731 with English translation thereof.
Written Opinion mailed Feb. 14, 2012 in corresponding PCT International Application No. PCT/JP2011/075731.

* cited by examiner

*Primary Examiner* — Tse Chen
*Assistant Examiner* — Hien Nguyen
(74) *Attorney, Agent, or Firm* — Ostrolenk Faber LLP

(57) ABSTRACT

A treatment apparatus includes an ultrasonic vibration source, an ultrasonic treatment portion which is configured to treat living tissue by ultrasonic vibration transmitted from the ultrasonic vibration source, and a micrograin feeder which is configured to supply liquid containing micrograins to between the ultrasonic treatment portion and the living tissue. Whole micrograins within the micrograin-containing solution has a grain size equal to or smaller than an amplitude of the ultrasonic vibration.

13 Claims, 11 Drawing Sheets

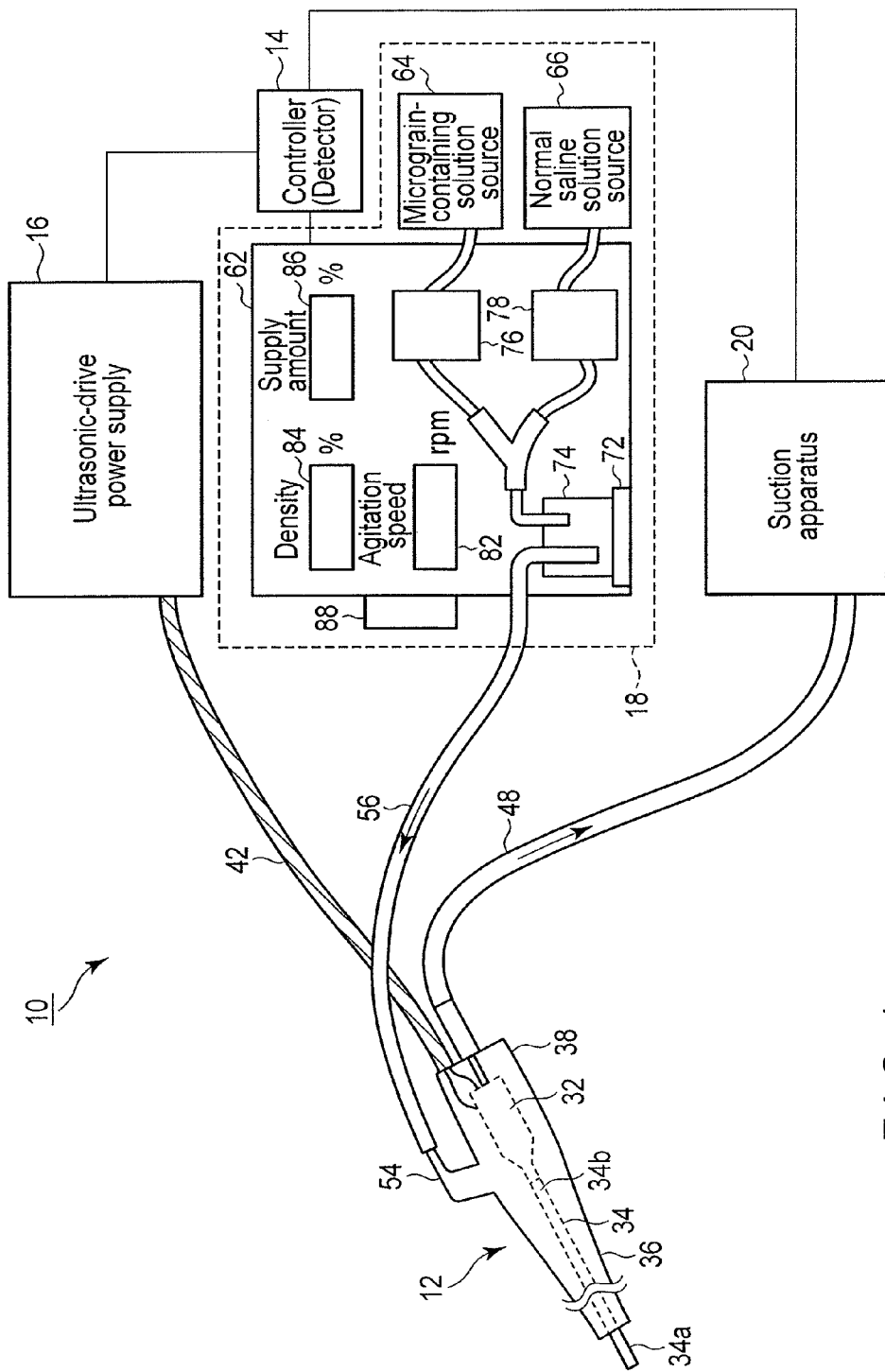
F I G. 1

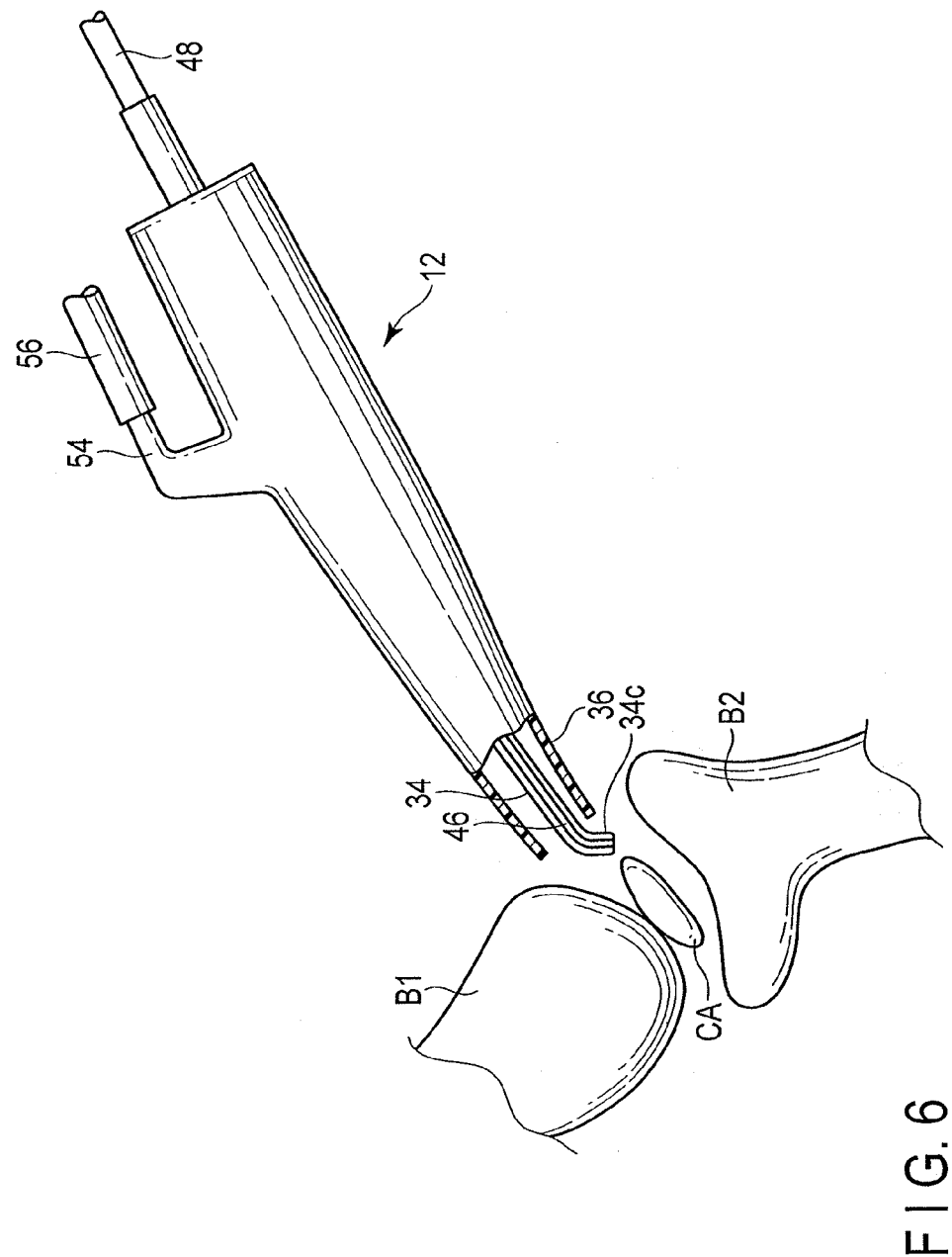
F I G. 6

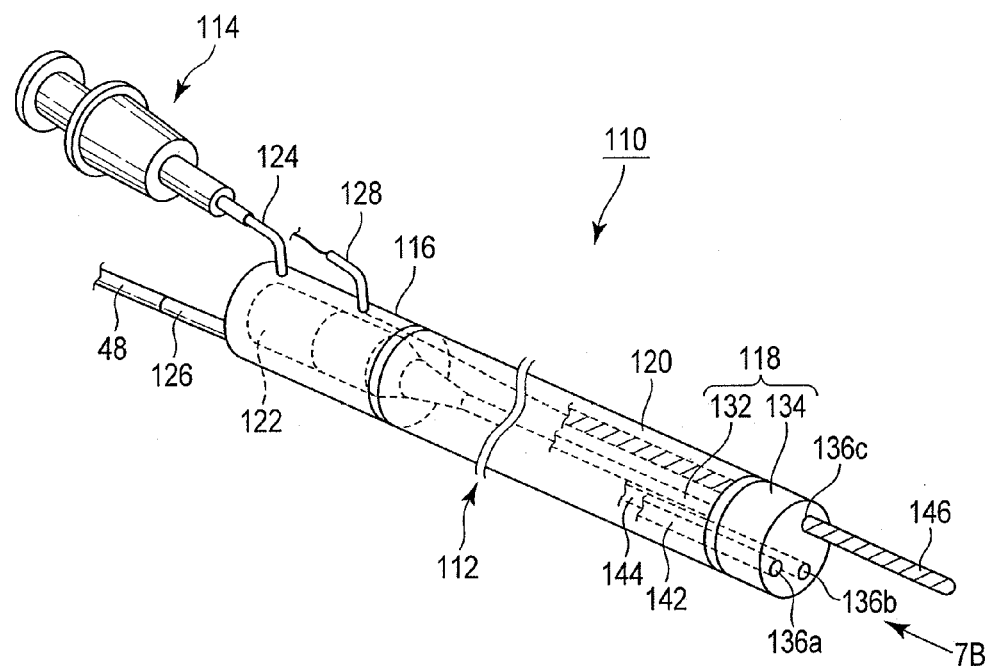
F I G. 7A
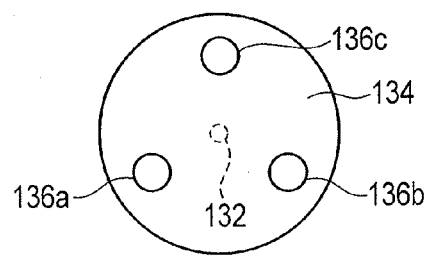
F I G. 7B

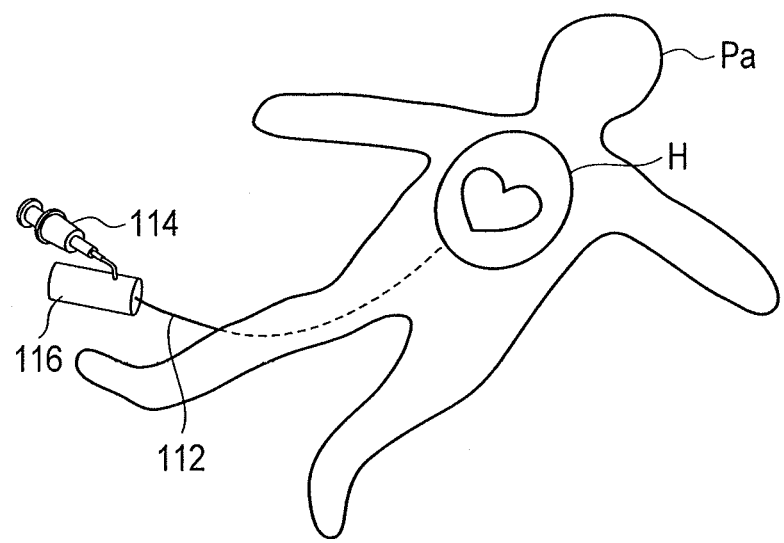
F I G. 8A
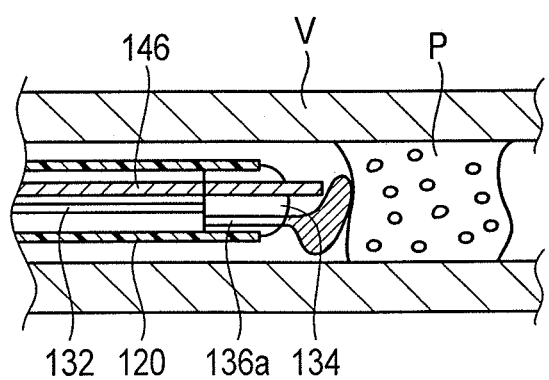
F I G. 8B

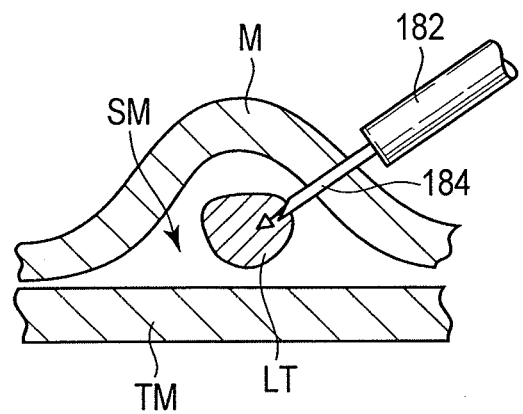
F I G. 10A
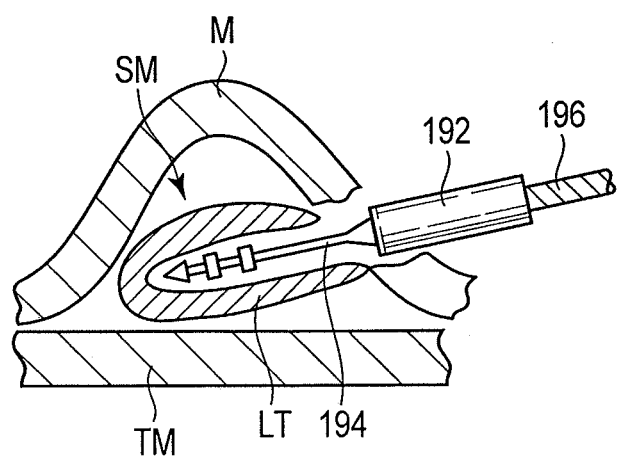
F I G. 10B

MEDICAL APPARATUS

CROSS-REFERENCE TO RELATED APPLICATIONS

This is a Continuation Application of PCT Application No. PCT/JP2011/075731, filed Nov. 8, 2011, and based upon and claiming the benefit of priority from prior U.S. Provisional Application No. 61/412,143, filed Nov. 10, 2010, the entire contents of which are incorporated herein by reference.

BACKGROUND OF THE INVENTION

1. Field of the Invention

The present invention relates to a treatment apparatus and an ultrasonic treatment method to treat living tissue using ultrasonic vibration.

2. Description of the Related Art

For example, Jpn. Pat. Appln. KOKAI Publication No. 2002-58679 discloses an ultrasonic treatment instrument which includes an ultrasonic probe made of titanium alloy having excellent vibration transmissibility and excellent tolerance in fatigue strength. The ultrasonic treatment instrument has a suction path on a center axis of the ultrasonic probe.

For example, the specification of U.S. Pat. No. 4,922,902 discloses that an irrigation fluid source is positioned at a higher level by 1 or 2 meters than the ultrasonic treatment instrument.

For example, Jpn. Pat. Appln. KOKAI Publication No. 2003-10201 discloses an ultrasonic treatment instrument which uses a pipe made of superelastic alloy based on nickel-titanium as a probe to transmit ultrasonic waves.

BRIEF SUMMARY OF THE INVENTION

According to a first aspect of the present invention, there is provide a medical apparatus includes an ultrasonic vibration source; an ultrasonic treatment portion which is configured to treat living tissue by ultrasonic vibration transmitted from the ultrasonic vibration source; and a micrograin feeder which is configured to supply liquid containing micrograins to between the ultrasonic treatment portion and the living tissue.

Advantages of the invention will be set forth in description which follows, and in part will obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing a treatment apparatus according to a first embodiment;

FIG. 6 is a schematic longitudinal-sectional view showing removal of cartilage by use of an ultrasonic treatment instrument in a treatment apparatus according to a second embodiment;

FIG. 7A is a schematic view showing an ultrasonic treatment instrument in a treatment apparatus according to the first embodiment;

FIG. 7B is a front view of a tip of the ultrasonic treatment instrument in the surgical operation apparatus according to the third embodiment;

FIG. 8A is a schematic view showing guidance of the tip of the ultrasonic treatment instrument in the treatment apparatus from a leg to a heart through a blood vessel, according to the third embodiment;

FIG. 8B is a schematic longitudinal sectional view showing a state in which a liquid containing micrograins is provided between the tip and plaque, with the tip of the ultrasonic treatment instrument in the treatment apparatus made face the plaque in the blood vessel in the heart, according to the third embodiment;

FIG. 10A is a schematic view showing a state in which a liquid containing micrograins is locally injected into a submucosa by using an injection needle of the surgical operation apparatus according to the fourth embodiment;

FIG. 10B is a schematic view showing a state of ablating a mucosa and the submucosa by using an ultrasonic treatment instrument in the treatment apparatus according to the fourth embodiment;

DETAILED DESCRIPTION OF THE INVENTION

Figure 2:
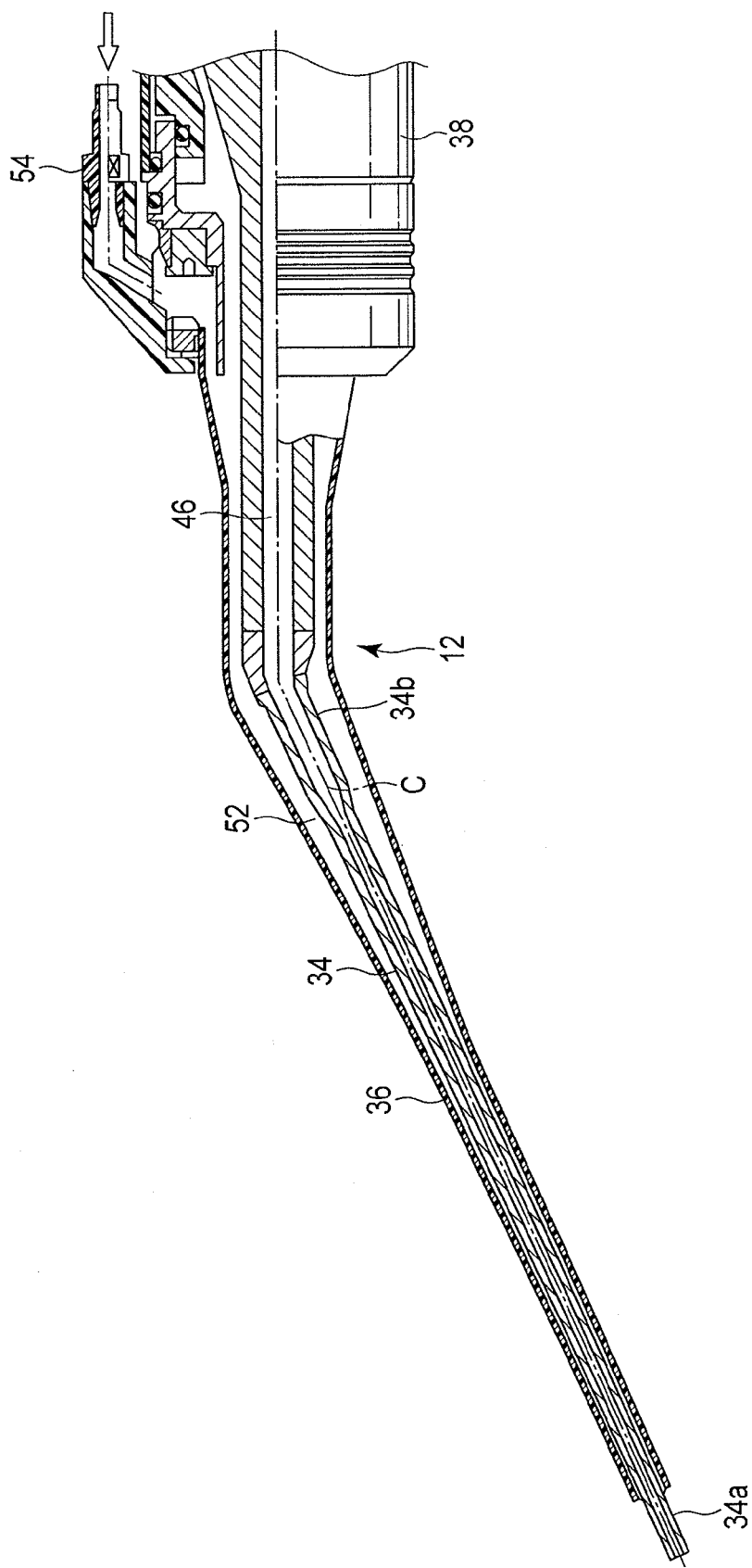
FIG. 2 is a schematic longitudinal-sectional view showing an ultrasonic treatment instrument in the treatment apparatus according to the first embodiment.

Hereinafter, embodiments of practicing the invention will be described with reference to the drawings.

The first embodiment will be described with reference to FIGS. 1 to 5B.

As shown in FIG. 1, a treatment apparatus 10 according to the present embodiment includes an ultrasonic treatment instrument 12, a controller, an ultrasonic-drive power supply 16, a liquid feeder (micrograin feeder) 18, and a suction apparatus 20. The controller 14 is connected to each of the ultrasonic treatment instrument 12, ultrasonic-drive power supply 16, liquid feeder 18, and suction apparatus 20, and controls the ultrasonic treatment instrument 12, power supply 16, liquid feeder 18, and suction apparatus 20. As shown in FIG. 1, the controller 14 may be provided independently or provided on any of the ultrasonic-drive power supply 16, liquid feeder 18, and suction apparatus 20.

As shown in FIGS. 1 and 2, the ultrasonic treatment instrument 12 includes an ultrasonic transducer 32 which is electrically connected to the ultrasonic-drive power supply 16 and serves as a ultrasonic vibration source, a hard-metal-made probe (ultrasonic treatment portion) 34 which has a proximal end in contact with the ultrasonic transducer 32 and to which a ultrasonic wave is transmitted, a sheath 36 which covers the probe 34, and a holder 38 provider at a proximal end of the sheath 36. The probe 34 has excellent vibration transmissibility and high fatigue strength, and is made of, for example, titanium alloy.

The ultrasonic-drive power supply 16 and ultrasonic transducer 32 can be attached to and detached from each other by a power supply cable 42. For example, a bolt-clamped Langevin type transducer which is resonant with a half wave ($\lambda/2$) is used as the ultrasonic transducer 32, and converts electric energy applied from the ultrasonic-drive power supply 16 through the power supply cable 42 into mechanical energy in form of ultrasonic vibration. Though not shown, for example, the ultrasonic transducer 32 is configured by layering alternately piezoelectric elements and electrode plates, providing a bolt to penetrate the layered piezoelectric elements and electrode plates, and further sandwiching the elements and the plates between a front-mounted plate and a nut from two end sides of the bolt.

The probe 34 is formed in a substantially rod-like shape, having a distal end portion 34a to be brought into contact with living tissue LT, and a proximal end portion 34b in contact with the ultrasonic transducer 32. On a center axis C of the probe 34, a channel 46 is formed to penetrate from the distal end portion 34a to the proximal end portion 34b, and is connected to the suction apparatus 20 by a suction tube 48. The sheath 36 is formed in a cylindrical form and made of resin material. Further, gap between an outer circumferential surface of the probe 34 and an inner circumferential surface of the sheath 36 is formed as a liquid supply channel 52 for supplying a liquid. The holder 38 supports the ultrasonic transducer 32 connected to the probe 34. The holder 38 includes a pipe sleeve 54 connected to the liquid supply channel 52. The pipe sleeve 54 is connected to the liquid feeder 18 by a liquid supply tube 56.

The liquid supply tube 56 can be attached to and detached from the liquid feeder 18 and the pipe sleeve 54 of the ultrasonic treatment instrument 12. The suction tube 48 can be attached to and detached from the suction apparatus 20 and the suction channel 46 of the ultrasonic treatment instrument 12.

Although this embodiment has described the channel 46 for suction, the channel 46 may be used for supplying a liquid containing micrograins.

As shown in FIG. 1, the liquid feeder 18 includes an irrigation unit (density adjuster) 62, a micrograin-containing solution source 64, and a normal saline solution source 66. An agitation table 72 is provided inside the irrigation unit 62. In a container 74 on the agitation table 72, micrograin-containing liquid and normal saline solution are mixed, and solution density is adjusted. An agitation speed of a solution (in which micrograins are dispersed), a density of the solution, and a supply amount of the solution per unit time can be appropriately set by a user (for example, a doctor).

In the irrigation unit 62, there are provided a micrograin-containing solution supply source (micrograincontaining solution supply pump) 76 which draws and supplies the micrograin-containing solution from the micrograin-containing solution source 64 into the container 74 on the agitation table 72, and a normal saline solution supply source (physiologic-salt-solution supply pump) 78 which draws and supplies the normal saline solution from the normal saline solution source 66 into the container 74 on the agitation table 72. Supply amounts to the container 74 from the supply sources 76 and 78 are controlled by the controller 14. Specifically, densities are adjusted by starting and stopping supply of the micrograin-containing solution and the normal saline solution from the supply sources 76 and 78.

On a surface of a housing of the irrigation unit 62, there are provided an agitation speed indicator 82 which displays an agitation speed of the solution on the agitation table 72, a density indicator 84 which displays a density of the solution to be supplied to the ultrasonic treatment instrument 12, a supply amount indicator 86 which displays a solution supply amount to be supplied to the ultrasonic treatment instrument 12 per unit time, and so on. The agitation speed indicator 82, the concentration indicator 84, and the supply amount indicator 86 are controlled by the controller 14.

The agitation speed of the solution, densities o the micrograin-containing solution and normal saline solution in the container 74, and supply amount of the solution can be set by a setting panel 88 of the irrigation unit 62 which is controlled by the controller 14. That is, the setting panel 88 functions as an agitation speed setting device, a density setting portion, and a supply amount setting portion. The information set by the setting panel 88 and the information at the present moment are displayed on the agitation speed indicator 82, the density indicator 84, and the supply amount indicator 86.

Further, the solution in micrograin-containing solution source 64 may be a solution (liquid) which includes micrograins of alumina ($Al_2O_3$), titanium dioxide ($TiO_2$), diamond, magnesium oxide ($MgO$), or barium sulfate ($BaSO_4$) etc.

As will be described later, the controller 14 forms a detector to detect a cavitation amount by measuring frequency spectral distribution of a voltage signal Sv for each frequency, in cooperation with the probe 34, the ultrasonic transducer 32, and ultrasonic-drive power supply 16.

Next, operation of the surgical operation apparatus 10 according to the present embodiment will described.

Figure 3A:
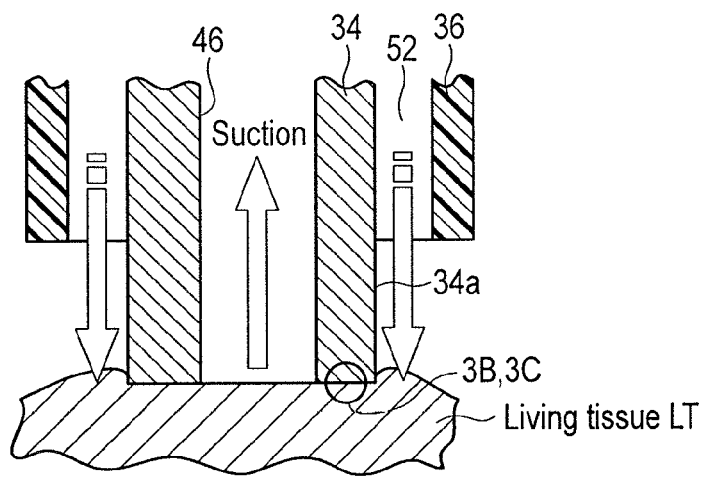
FIG. 3A is a schematic longitudinal sectional view showing a tip end of a probe of the ultrasonic treatment instrument in the treatment apparatus according to the first embodiment.
Figure 3B:
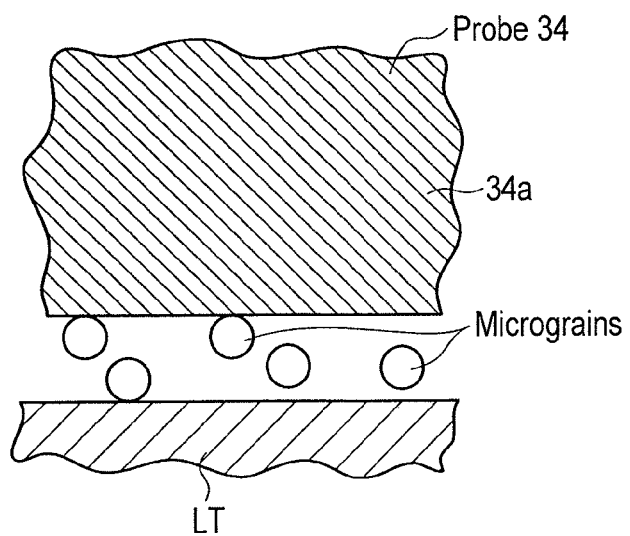
FIG. 3B is a schematic longitudinal sectional view showing a state in which micrograins are provided between the probe and living tissue by supplying a liquid containing micrograins from between the probe and a sheath when the tip end of the probe of the ultrasonic treatment instrument in the treatment apparatus is made face the living tissue, according to the first embodiment.
Figure 3C:
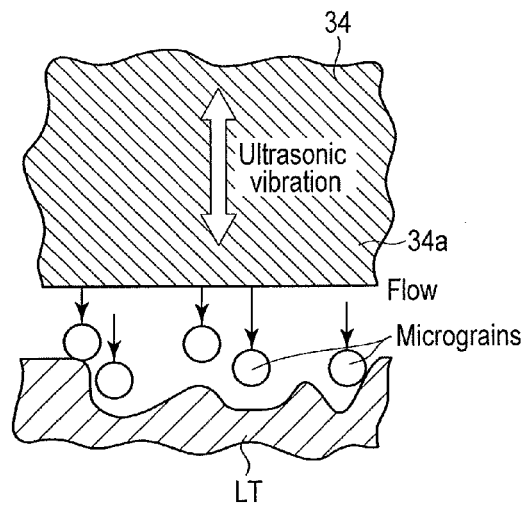
FIG. 3C is a schematic longitudinal sectional view showing a state in which micrograins are made collide at high speed with the living tissue by ultrasonically vibrating the probe with micrograins provided between the probe and the living tissue, with the liquid containing micrograins supplied from between the probe and the sheath when the tip end of the probe of the ultrasonic treatment instrument in the treatment apparatus is made face the living tissue, according to the first embodiment.

As shown in FIG. 3A, the tip end of the probe 34 is pressed to the living tissue LT. A liquid (solution) containing micrograins is supplied along the probe 34 between the probe 34 and the sheath 36. Then, as shown in FIG. 3B, micrograins enter into between the tip end of the probe 34 and the living tissue LT. In this state, the ultrasonic transducer 32 is vibrated. Since at this time, micrograins exist between the tip end of the probe 34 and the living tissue LT, as shown in FIG. 3C, the micrograins collide with the living tissue LT at high speed as the probe 34 vibrates. Therefore, cavitation can be caused efficiently in the living tissue LT.

Accordingly, cavitation can be easily caused in the living tissue LT by using micrograins even when cavitation is difficult to cause without using micrograins, for example, when the distal end portion 34a of the probe 34 vibrates with a small amplitude or at a high frequency. Thus, since the probe 34 ultrasonically vibrates to make micrograins between the probe 34 and the living tissue LT collide with the living tissue LT at high speed, cavitation can be caused in an earlier stage compared with a case of using a solution not containing micrograins.

Figure 4:
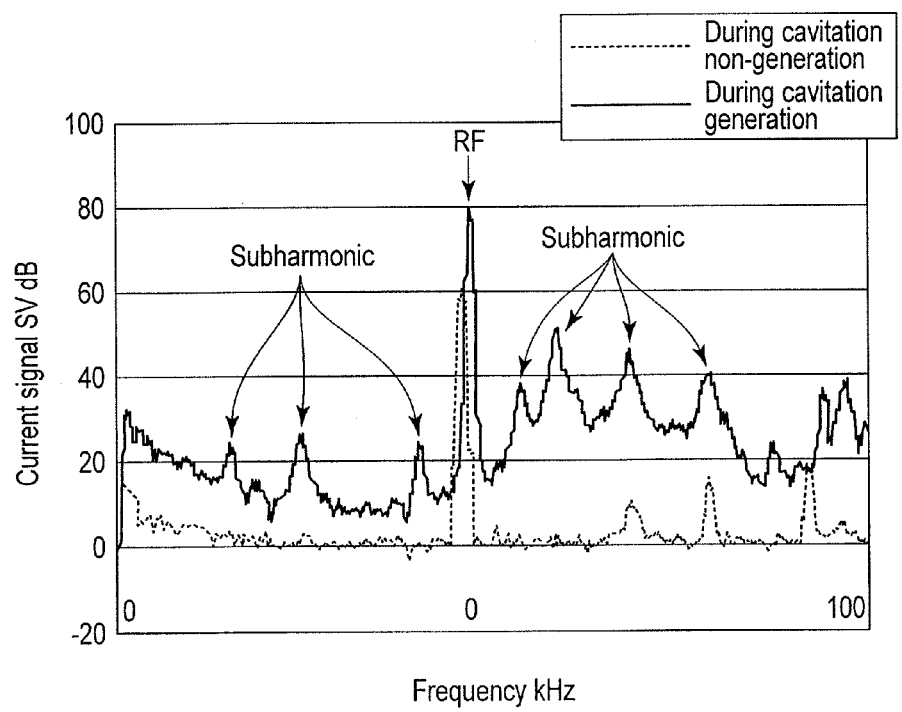
FIG. 4 shows frequency spectral distributions of voltage signals at each frequency when cavitation is not caused and when cavitation is caused.

FIG. 4 shows frequency spectral distribution of voltage signal Sv when the probe 34 is vibrated by the ultrasonic transducer 32 without causing cavitation in living tissue LT (when no cavitation is caused) and when cavitation is created in the living tissue LT by using micrograins (when cavitation is caused). In FIG. 4, the resonant frequency RF is 47 kHz. Regardless of presence or absence of occurrence of cavitation, the voltage signal Sv has the greatest peak at the resonant frequency RF (47 kHz).

When cavitation is not caused, there is no conspicuous peak at other frequencies than the resonant frequency RF, as indicated by a broken line in FIG. 4. In contrast, when cavitation is caused, the level thereof is higher than when no cavitation is caused, at frequencies other than the resonant frequency RF, as indicated by a continuous line in FIG. 4. Specifically, when cavitation is caused, detected levels of harmonic (subharmonic generation) at aliquots such as ½ and ¼ of the resonant frequency RF or at differential frequencies thereof are considerably higher than when no cavitation is caused, and detected levels of frequency components at other frequencies than the harmonic are also higher, than when no cavitation is caused. Therefore, the controller (detector) 14 can detect cavitation generation levels (cavitation amounts) by detecting signal levels except for vicinity of the resonant frequency RF for the voltage signal Sv.

Hereinafter, a case of actually treating the living tissue LT will be described.

The operation panel 88 of the liquid feeder 18 is operated to set, in advance, an agitation speed for a solution containing micrograins, a concentration thereof, and a supply amount per unit time thereof. Further, the solution having a set density is poured in the container 74 on the agitation table 72, and is agitated at the set agitation speed in advance.

At first, the tip end of the probe 34 of the ultrasonic treatment instrument 12 is put close to the living tissue LT as a treatment target. In this state, an instruction to vibrate is given from the ultrasonic-drive power supply 16, the controller 14 supplies the liquid containing micrograins from the liquid feeder 18 toward the tip end of the probe 34, immediately then (for example, after one or two seconds), the ultrasonic transducer 32 is started to vibrate. At this time, the solution is supplied in match with the supply amount per unit time, which has been set on the operation panel 88. Therefore, as shown in FIG. 3B, micrograins enter into between the tip end of the probe 34 and the living tissue LT, and the probe 34 thereafter vibrates. Therefore, cavitation is caused in the living tissue LT by high-speed movement of the micrograins owing to vibration of the distal end portion 34a of the probe 34.

Further, the suction apparatus 20 is operated at the same time when ultrasonic vibration occurs or after the ultrasonic vibration stops. The solution containing the micrograins can be collected through the channel 46 and the suction tube 48. At this time, the living tissue LT in which cavitation is caused can be collected together.

The ultrasonic treatment instrument 12 has tissue selectivity, parenchymatous tissues such as adipose are easily emulsified and fibrous tissues are easily crushed. As the density of the micrograins rises, the treatment performance improves, and fibers are cut more easily.

As has been described above, since the cavitation amount can be increased by providing the micrograins between the probe 34 and the living tissue LT when the living tissue LT is subjected to ultrasonic treatment, ultrasonic treatment instrument can shorten vibration time of the ultrasonic transducer 32. Therefore, the surgical operator can perform a surgical operation on a patient in a shorter time. In addition, since the density of micrograins can be set in compliance with a treatment target by using the operation panel 88, a treatment can be securely achieved.

Although the present embodiment uses alumina ($Al_2O_3$) (alumina-based grains) as the micrograin of the micrograin-containing solution supply source 76, any granular substance that is not toxic to a living body can be used, such as, silicon dioxide ($SiO_2$) (silica-based grains), titanium dioxide ($TiO_2$) (titanium-based grains), magnesium oxide (MgO) (magnesium-based grains), barium sulfate ($BaSO_4$) (barium-based grains), or diamond grains, etc., otherwise, these substances can be appropriately mixed for use.

The present embodiment has been described supposing that the treatment apparatus 10 includes the liquid feeder 18 controlled by the controller 14, a syringe (not shown) for liquid supply connected to the liquid supply tube 56, which has been supplied with a solution containing micrograins at a specific concentration, may be preferably connected in place of the liquid feeder 18.

Figure 5A:
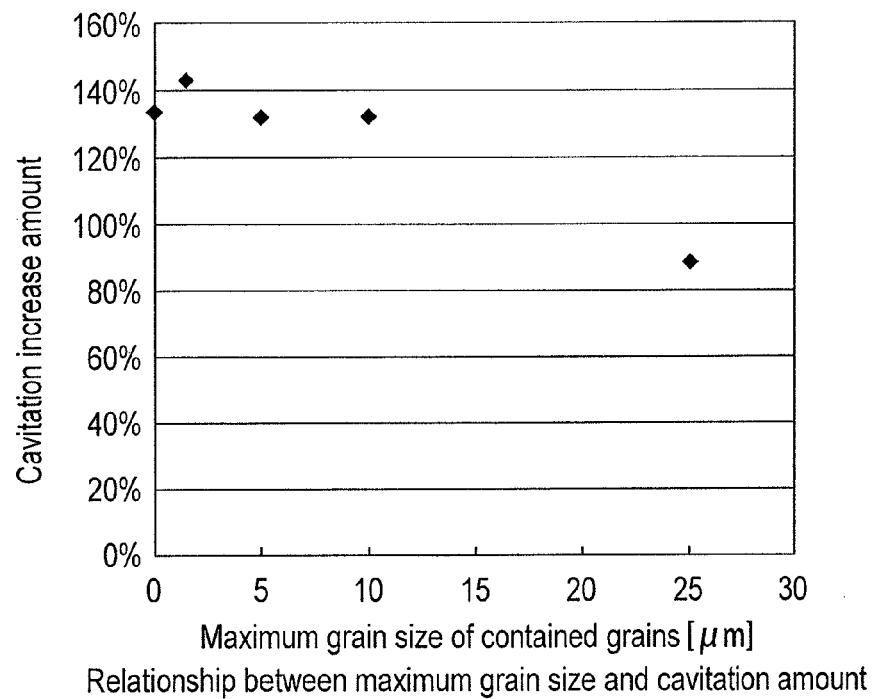
FIG. 5A shows a relationship between a maximum grain size and a cavitation increase amount.
Figure 5B:
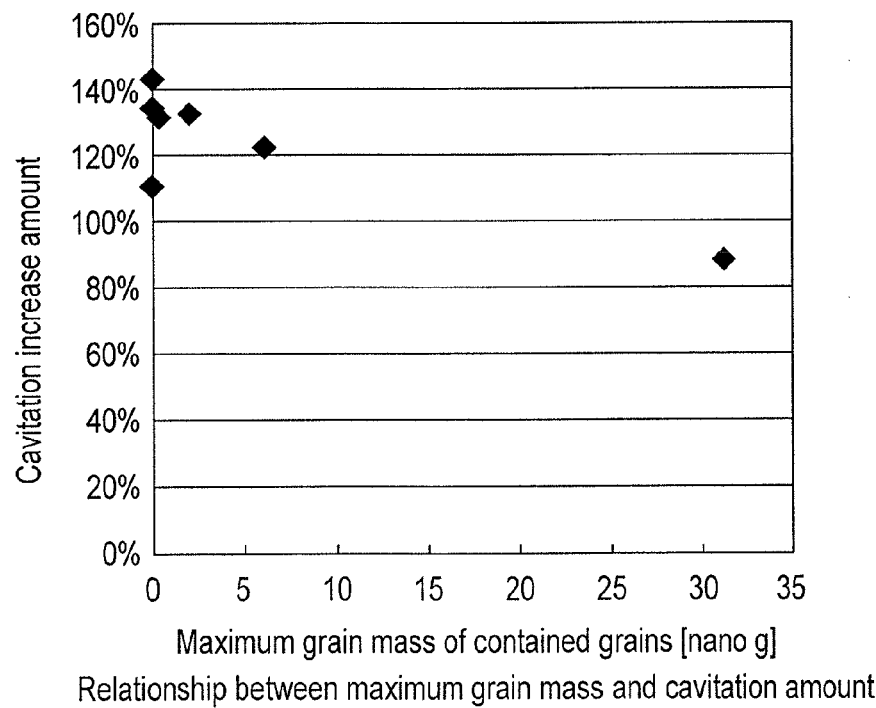
FIG. 5B shows a relationship between a maximum grain mass and a cavitation increase amount.

Meanwhile, FIG. 5A shows a relationship between the maximum grain size and the cavitation amount, according to an experiment, FIG. 55 shows a relationship between the maximum diameter and maximum mass grain and the cavitation amount, according to the experiment. In FIGS. 5A and 5B, "100%" refers to inclusion of no micrograin. As shown in FIG. 5A, when the maximum grain size of micrograins is 10 μm or less, an increase rate of the cavitation amount is experimentally recognized to be higher than when the grain size is greater than the maximum grain size. As shown in FIG. 5B, when the maximum mass of micrograins is 6 ng or less, the increase rate of the cavitation amount is experimentally recognized to be higher than when the grain mass is greater than the maximum mass. Therefore, the micrograins used for an ultrasonic treatment preferably have a grain size of 10 μm or less and a mass of 6 ng or less, though depending on experimental conditions such as a resonant frequency and an amplitude. Normally, the ultrasonic transducer 32 has, for example, a resonant frequency of 20 to 100 kHz, in the present embodiment, the resonant frequency is about 98 kHz, and the amplitude is about 20 μm.

As shown in FIG. 5A, when the maximum grain size is 25 μm, the cavitation amount is recognized to decrease compared with inclusion of no grain. In this experiment, the amplitude of the ultrasonic transducer 32 is 20 μm, when there are grains having a greater grain size than the amplitude, generation and growth of cavitation can possibly be recognized to be hindered. Therefore, the grain size of the micrograins is preferably equal to or smaller than the amplitude of ultrasonic vibration.

As shown in FIG. 5B, when the maximum mass is 30 ng, the cavitation amount is recognized to decrease compared with inclusion of no grain. This is because, if there are grains having a greater mass, the grains are going to stay at their own positions due to own weights of the grains and consequently hinder generation and growth of cavitation even when the probe 34 ultrasonically vibrates. As a result, the cavitation amount is considered to have decreased.

The second embodiment will be described with reference to FIG. 6. The present embodiment is a modification to the first embodiment.

In the present embodiment, a distal end portion of a probe 34 differs from the distal end portion 34a of the probe 34 in the first embodiment.

The distal end portion 34c of the probe 34 in the present embodiment is bent at approximately 60 to 90 degrees near the tip end thereof. Other structures are the same as those of the first embodiment.

Operation of the surgical operation apparatus 10 according to the present embodiment will be described. Here, descriptions will be made of use in a surgical operation of removing cartilage CA in a joint.

As shown in FIG. 6, the probe 34 is bent near the distal end portion 34c in order to facilitate accessibility to the cartilage CA existing between bones B1 and B2. Further, the distal end portion 34c of the probe 34 is brought into contact with the cartilage CA. Then, a liquid containing micrograins is supplied between the distal end portion 34c of the probe 34 and the cartilage CA. In this state, the ultrasonic transducer 32 is vibrated to further vibrate the probe 34. Therefore, the micrograins collide with the cartilage CA at high speed and cause thereby cavitation to grow. That is, the cartilage CA is pruned by the distal end portion 34c of the probe 34. Further, the cartilage CA and the liquid containing micrograins are suctioned through the channel 46 on the center axis C of the probe 34. Therefore, the cartilage CA is removed.

In this case, a cavitation amount of the ultrasonic treatment can be increased by using a liquid containing micrograins. Therefore, the speed of scraping the cartilage CA can be improved in comparison with non-use of the liquid containing micrograins. Accordingly, the surgical operation can be finished within a shorter time. In addition, since ultrasonic vibration is employed, burrs hardly appear even if the cartilage CA is removed.

The third embodiment will be described with reference to FIGS. 7A to 8B. The present embodiment is a modification to the first and second embodiments.

As shown in FIG. 7A, a surgical operation apparatus 110 according to the present embodiment includes an ultrasonic treatment instrument 112 and a syringe (micrograin feeder) 114 as a micrograin-containing solution source. That is, the present embodiment uses neither the controller 14 nor the liquid feeder 18 as described in the first and second embodiments.

The ultrasonic treatment instrument 112 includes holder 116, an ultrasonic transmission member (ultrasonic treatment portion) 118, and a cover tube 120. The holder 116 is a portion held by a user, is provided with an ultrasonic transducer (ultrasonic vibration source) 122 in the holder, and is detachably connected to the syringe 114 by a mouth ring 124. A proximal end of a suction tube 144 described later is connected to the holder 116, which is provided with a mouth ring 126 for suction, to be connected to an external suction tube 48 (see FIG. 1) directly connected to a suction apparatus 20 The holder 116 is further provided with a mouth ring 128 through which guide wire (guide portion) 146 is extended out of guide wire insertion hole (third opening) 136c of a tip 134 described later through inside the cover tube 120.

The ultrasonic transmission member 118 includes a flexible wire member 132 and the tip (ultrasonic treatment portion) 134 fixed to a distal end of the flexible wire member 132.

In the present embodiment, for example, in place of the probe 34 made of titanium alloy described in the first embodiment, flexible material such as nickel-titanium alloy (nitinol) used for shape-memory alloy and superelastic alloy is used for the ultrasonic transmission member 118. Further, the hard tip 134 is fixed to the distal end of the flexible wire member 132.

The ultrasonic transducer 122 is provided at a proximal end of the ultrasonic vibration transmission member 118. When the ultrasonic transducer 122 vibrates, ultrasonic vibration is transmitted to the tip 134 through the flexible wire member 132.

The tip 134 is formed, for example, in a substantial disc shape or a substantially columnar shape, and preferably has a tip end which is formed, for example, in a semi-spherical shape. The distal end of the flexible wire member 132 is preferably fixed on the center axis C of the tip 134. However, the flexible wire member 132 may be fixed at a position shifted from the center axis C of the tip 134.

The cover tube 120 is formed in a cylindrical shape, and has a distal end fixed to an outer circumferential surface of the tip 134, and a proximal end fixed to an outer or inner circumferential surface of the holder 116. The cover tube 120 is made of resin material such as fluorine resin, for example, PTFE.

Further, three openings 136a, 136b, and 136c are formed in the tip 134. These first to third openings 136a, 136b, and 136c are formed at equal distances and at equal angles to each other in relation to the center of the tip 134. That is, preferably, the first to third openings 136a, 136b, and 136c respectively have centers at vertexes of, for example, an equilateral triangle.

A distal end of a water supply tube 142 is fixed to the first opening 136a (water supply hole). A distal end of a suction tube 144 is fixed to the second opening 136b (suction hole). The guide wire 146 can be inserted through the third opening (guide wire insertion hole) 136c.

A proximal end of the water supply tube 142 is connected to the mouth ring 124 of the holder 116. Therefore, a liquid containing micrograins can be supplied into living tissue LT through the syringe 114, the mouth ring 124 of the holder 116, the water supply tube 142, and the first opening 136a of the tip 134. That is, the first opening 136a of the tip 134 functions as a liquid feeder. Further, the proximal end of the suction tube 144 is connected to the suction apparatus 20 (see FIG. 1) through the mouth ring 126 of the holder 116 and the external suction tube 48 of the ultrasonic treatment instrument 112. Therefore, the liquid containing micrograins and plaque P can be suctioned by the suction apparatus 20 through the second opening 136b of the tip 134, the suction tube 144, the mouth ring 126 of the holder 116, and the external suction tube 48 outside the ultrasonic treatment instrument. Further, the guide wire 146 is inserted into the ultrasonic treatment instrument 112 through the third opening 136c and the mouth ring 128 of the holder 116. Therefore, the distal end of the guide wire 146 can be inserted to the plaque P in a blood vessel V. The tip 134 can be guided to a position opposed to the plaque P along the guide wire 146.

Alumina powder of 1 μm is preferably used as micrograins supplied into the liquid through the syringe 114.

Next, operation of the treatment apparatus 110 according to the present embodiment will be described with reference to removal of plaque P, for example, in a blood vessel V in a heart H.

An appropriate liquid containing micrograins is inserted into the syringe 114.

As shown in FIG. 8A, for example, the tip end of the guide wire 146 is introduced from a blood vessel of a leg of a patient Pa until the tip end of the guide wire 146 faces the plaque P inside the blood vessel V in the heart H. With the tip end of the guide wire 146 maintained unmoved, the proximal end of the guide wire 146 is inserted into the third opening 136c of the tip 134, and the tip 134 of the ultrasonic treatment instrument 112 is moved toward the plaque P. Further, as shown in FIG. 8B, the tip 134 is set close to the plaque P in the blood vessel V.

In this state, the tip end of the guide wire 146 is pulled out through the third opening 136c of the tip 134. Further, the syringe 114 is connected to the mouth ring 124 of holder 116 of the ultrasonic treatment instrument 112. The liquid containing micrograins is ejected out of the tip 134 from the syringe 114 through the mouth ring 124 and the water supply tube 142.

The ultrasonic transducer 122 is vibrated to transmit ultrasonic vibration to the tip 134 through the flexible wire member 132. Therefore, micrograins between the tip 134 and the plaque P collide with the plaque P at high speed, and causes cavitation to occur in the plaque P. In this manner, the plaque P is removed.

Meanwhile, the suction apparatus 20 is operated to suction the plaque P and liquid containing micrograins ejected into the blood vessel V, through the second opening (suction hole) 136b, the suction tube 144, the mouth ring 126 of the holder 116, and the suction tube 48 outside the ultrasonic treatment instrument 112 to the suction apparatus 20 (see FIG. 1).

In the present embodiment, cavitation is caused by making the micrograins collide with the plaque P in the blood vessel V at high speed by ultrasonic vibration. Further, even if the flexible wire member 132 is difficult to transmit ultrasonic vibration, cavitation occurrence performance can be improved greatly, and therefore, not only soft plaque but also hard plaque can be removed. Since treatment is carried out by ultrasonic vibration, parenchymatous tissue such as fat can be easily emulsified while fibrous tissue such as the blood vessel V is difficult to be crushed. Therefore, the blood vessel V can be preserved. Accordingly, the ultrasonic treatment instrument 112 which uses micrograins in treatment on living tissue can significant advance treatment performance while improving safety.

The present embodiment has been described with reference to an example in which the flexible wire member 132 of the vibration transmission member 118 is formed to be of a rod type, and the suction tube 144 is provided separately from the vibration transmission member 118. The vibration transmission member 118 is preferably formed in a cylindrical shape having a suction channel on the center axis C (see FIG. 2).

Also, the present embodiment has been described with reference to an example in which the guide wire 146 is introduced from a leg toward the heart H. However, the guide wire 146 may be introduced from an arm toward the heart H.

Next, the fourth embodiment will be described with reference to FIGS. 9 to 10. The present embodiment is a modification to the first to third embodiments.

The surgical operation apparatus 210 includes an endoscope 152, an injection needle (micrograin feeder as a micrograin-containing liquid source) 154, and an ultrasonic treatment instrument 156. Also, the present embodiment uses neither the controller 14 nor the liquid feeder 18 as described in the first and second embodiments.

The endoscope 152 includes an insertion portion 162 and an operation portion 164. The insertion portion 162 includes a hard tip end portion 172, a bending portion 174, and a flexible portion 176 in this order from a distal end side of the insertion portion 162 toward a proximal end side thereof. An observation optical system and a channel are formed in the insertion portion 162, though not shown. In the operation part 164, a channel port 178 communicating with the channel of the insertion portion 162 is formed.

The injection needle 154 includes a sheath 182 and a needle part 184 which is able to be taken in/out a distal end of the sheath 182. Though not shown, the liquid containing micrograins can be ejected from the tip end of the needle part 184.

That is, the injection needle 154 has a function as a liquid guide part. Further, with the needle part 184 inserted in the sheath 182, the injection needle 154 can be inserted from the channel port 178 of the endoscope 152 into the channel. Therefore, the distal end of the sheath 182 and the needle part 184 of the injection needle 154 can be protruded from the hard tip end part 172 of the insertion portion 162 of the endoscope 152. Accordingly, the liquid containing micrograins can be supplied into living tissue LT as a treatment target by the needle part 184 of the injection needle 154.

The ultrasonic treatment instrument 156 includes an ultrasonic transducer (ultrasonic vibration source) 192, a probe (ultrasonic treatment portion) 194, and a power supply cable 196. The probe 194 has a length of a ½ wavelength. The probe 194 is made of metal material such as titanium alloy. The disc shape part 194a may be formed to increase a contact area living tissue or may be formed in a simple shaft-like shape. Further, the ultrasonic treatment instrument 156 can be inserted into the channel from the channel port 178 of the endoscope 152. The power supply cable 196 is formed to be appropriately elastic in order that the ultrasonic treatment instrument 156 can be inserted into the channel of the endoscope 152. Therefore, when the power supply cable 196 is held and pressed into the channel port 178 of the endoscope 152, the tip end of the probe 194 moves toward the hard tip end part 172, and when the power supply cable 196 is pulled from the channel port 178, the tip end of the probe 194 comes close to the channel port 178.

Though not shown, living tissue can be suctioned by suction function using the channel of the endoscope 152.

Next, operation of the surgical operation apparatus 210 according to the present embodiment will be described.

At first, the hard tip end portion 172 of the insertion portion 162 of the endoscope 152 is provided at a position where the portion 172 faces a mucosa M of living tissue as a treatment target. In this state, the tip end of the needle part 184 of the injection needle 154 is punctured into the mucosa M of the living tissue, and is provided in a submucosa SM between the mucosa M and a tunica muscularis TM. Then, the liquid containing micrograins is locally injected into the submucosa SM through the injection needle 154. Therefore, as shown in FIG. 10A, the submucosa SM between the mucosa M and the tunica muscularis TM swells due to the liquid containing micrograins. Thereafter, the injection needle 154 is pulled out from the channel port 178, without moving the position of the hard tip end portion 172 of the insertion portion 162 of the endoscope 152.

In place of the injection needle 154, the ultrasonic treatment instrument 156 is inserted through the channel from the channel port 178, so as to make the tip end of the probe 194 face the mucosa M of the living tissue. In this state, the ultrasonic transducer 192 is vibrated to position the tip end o the probe 194 at the submucosa SM through the mucosa M. At this time, the micrograins collide with the living tissue at high speed owing to ultrasonic vibration of the probe 194, and cavitation is caused in the submucosa SM. Further, the mucosa M is separated in a substantially circular shape including the submucosa SM by moving the hard tip end portion 172 of the insertion portion 162 of the endoscope 152 or by moving the ultrasonic treatment instrument 156 in relation to the channel of the endoscope 152.

Incision or detachment of tissue by ultrasonic vibration has tissue selectivity. In the present embodiment, the tunica muscularis TM is hardly influenced, and therefore, resection or detachment capability for living tissue can be improved. That is, the tissue selectivity as a merit of incision or detachment of tissue by ultrasonic vibration does not depend on the cavitation amount. Therefore, excision performance can be improved by increasing occurrence of cavitation, maintaining the tissue selectivity of excising or resecting the mucosa M and the submucosa SM and conserving the tunica muscularis TM.

Further, the liquid containing micrograins and the living tissue where cavitation is caused are suctioned removed by using the endoscope 152. A detached tissue is removed by forceps through the channel of the endoscope 152.

Therefore, according to the present embodiment, treatment performance can be improved and safety of treatments can be improved, by performing an ultrasonic treatment with use of micrograins.

Figure 11A:
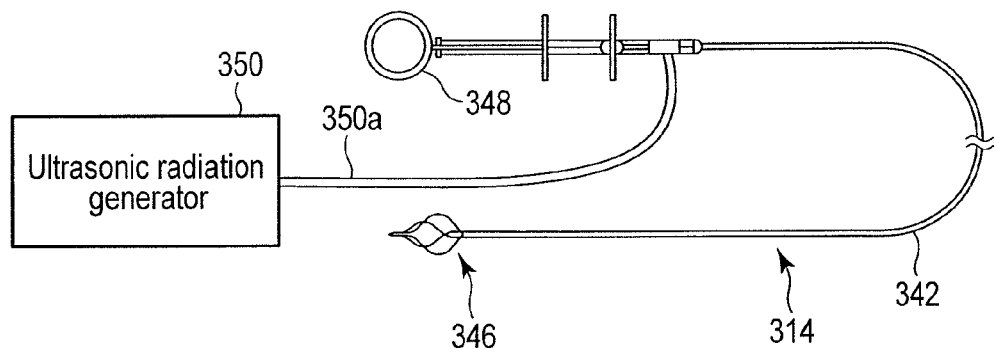
FIG. 11A is a schematic view showing a basket forceps in a treatment apparatus according to a fifth embodiment.
Figure 11B:
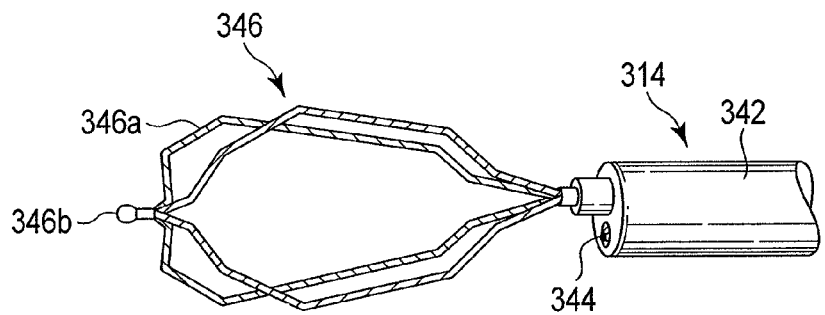
FIG. 11B is a schematic view showing an enlarged basket portion of the basket forceps of the treatment apparatus according to the fifth embodiment.
Figure 12:
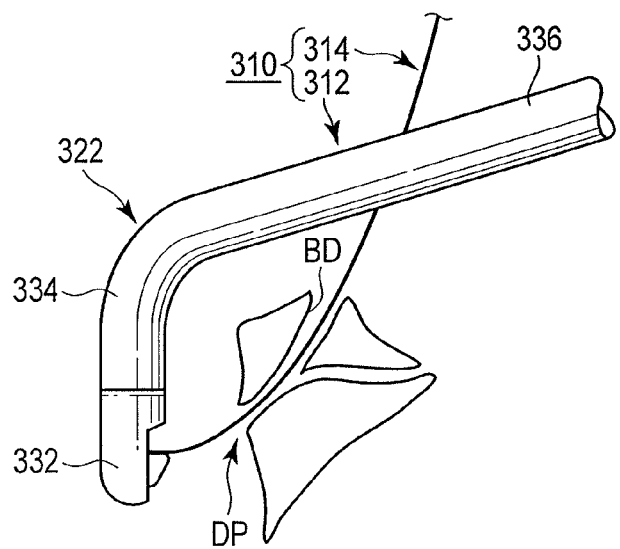
FIG. 12 is a schematic view showing a state in which the basket portion is introduced into a lumen from a duodenal papilla through a channel in a side-view-type endoscope in the surgical operation apparatus according to the fifth embodiment.

Next, the fifth embodiment will be described with reference to FIGS. 11A to 12. The present embodiment modification to the first to fourth embodiments.

A surgical operation apparatus 310 according to the present embodiment includes a side-view-type endoscope 312 (see FIG. 12), and an ultrasonic treatment instrument 314. According to the present embodiment, a liquid containing micrograins can be supplied to living tissue LT as a treatment target by for example, a syringe (a micrograin feeder as a micrograin-containing liquid supply source) through an unillustrated channel of the side-view-type endoscope 312. That is, the present embodiment also neither the controller 14 nor the liquid feeder 18 as described in the first and second embodiments. As the syringe according to the present embodiment, the syringe 114 (see FIG. 7A) described in the third embodiment can be used.

The side-view-type endoscope 312 includes an insertion portion 322 and an operation portion (not shown). The insertion portion 322 includes a hard tip end portion 332, a bending portion 334, and a flexible insertion portion 336 in this order from a distal end side of the thereof. An observation optical system and a channel in which an ultrasonic treatment instrument 314 is inserted are formed in the insertion portion 322, though not shown.

The ultrasonic treatment instrument 314 includes a sheath (insertion section) 342 inserted into the channel of the side-view-type endoscope ultrasonic treatment instrument (ultrasonic vibration source) 344, a basket section (calculus grasping section) 346 formed like a basket by four wires 346a, and an operation section 348. The operation section 348 is connected to an ultrasonic radiation generator (ultrasonic-vibration power supply) 350 through a power supply cable 350a. A radiopaque chip 346b is fixed to a tip end of the wire 346a of the basket section 346.

The basket section 346 is retractable into/from the tip end of the sheath 342 by operation of the operation section 348. Further, normally, when the basket section 346 is being set into the sheath 342 with calculus such as biliary calculus (not shown) provided in the basket section 346, the calculus is impressed with force and crushed.

As the ultrasonic treatment portion 344 is, for example, a piezoelectric element, a bolt-clamped Langevin type transducer (BLT), or a micromachined ultrasonic transducer (MUT) is fixed to the tip end of the sheath 342. the ultrasonic treatment portion 344 is positioned in contact with the calculus when the basket section 346 is being set into the sheath 342 with the calculus provided in the basket section 346. Further, when the ultrasonic treatment portion 344 is electrically conducted by the power-supply cable 350a from the ultrasonic radiation generator 350, the ultrasonic treatment portion 344 ultrasonically vibrates.

Figure 9:
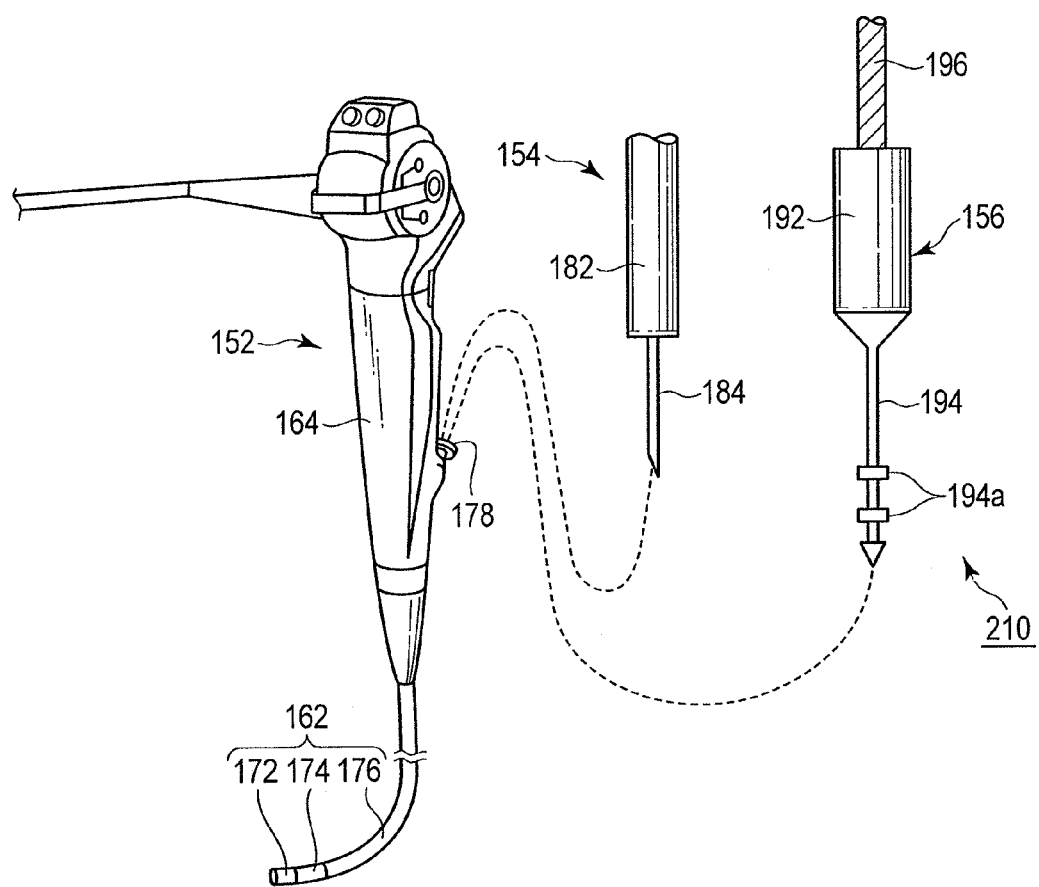
FIG. 9 is a schematic view showing a treatment apparatus according to a fourth embodiment.

As the ultrasonic treatment portion 344, for example, the same instrument as the ultrasonic treatment instrument 156 described in the fourth embodiment shown in FIG. 9 may be preferably used. In this case, the tip end of the probe 194 of the ultrasonic treatment instrument 156 is retractable into/from the tip end of the sheath 342.

Next, operation of the treatment apparatus 310 according to the present embodiment will be described.

When the calculus in a bile duct (lumen) BD is picked up from a duodenum papilla DP by using the side-view-type endoscope 312, the calculus is picked up after being crushed by the basket section 346. In the present embodiment, ultrasonic vibration is caused at the same time when the calculus is crushed by the basket section 346.

With the distal end portion of the insertion portion 322 of the side-view-type endoscope 312 made face the duodenum papilla DP, a catheter is inserted into the bile duct BD where the calculus exists, by using a guide wire (not shown), and for example, barium sulfate micrograins for X-ray contrast are coated on the calculus.

After pulling out the catheter, the basket section 346 is introduced toward the calculus in the bile duct BD by using the guide wire. At this time, X-ray is irradiated, then, the chip 346b of the basket section 346 and the calculus coated with barium sulfate micrograins can be observed. The calculus can be held by operating the basket section 346. Thus, when the basket section 346 is being pulled into the sheath 342, with the calculus provided in the basket section 346, by operating the operation portion 348, the ultrasonic treatment portion 344 makes contact with the calculus. Further, the ultrasonic treatment portion 344 is electrically conducted through the power-supply cable 350a from the ultrasonic radiation generator 350, the ultrasonic treatment portion 344 ultrasonically vibrates. That is, the ultrasonic treatment portion 344 also functions as an ultrasonic vibration source.

At this time, the calculus can be influenced by a greater damage owing to crush effect of making barium sulfate micrograins collide at high speed with the calculus, such as calcium carbonate calculus, and owing to effect of increasing cavitation by the ultrasonic treatment using micrograins. The calculus held by the basket section 346 can then be easily crushed. That is, crushing performance against the calculus can be improved by assisting effect of crushing the calculus by ultrasonic vibration with crushing power applied by the basket section 346.

The present embodiment has been described with reference to coating of barium sulfate micrograins on calculus by a catheter. However, a channel can be apposed with the basket section 346, and a liquid containing micrograins can be coated on the calculus through the channel immediately before ultrasonic vibration.

Also, the present embodiment has been described with reference to a structure in which the basket section 346 and the ultrasonic treatment section 344 are provided separately. However, the basket section 346 itself may be configured to be able to ultrasonically vibrate.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A medical apparatus comprising:
an ultrasonic vibration source;
an ultrasonic treatment portion which is configured to treat living tissue by ultrasonic vibration transmitted from the ultrasonic vibration source;

a micrograin feeder which is configured to supply micrograin-containing solution including micrograins between the ultrasonic treatment portion and the living tissue, the micrograin feeder including a micrograin-containing solution source which stores the micrograin-containing solution, a diluted solution source which stores diluted solution to dilute the micrograin-containing solution, a density adjuster which is configured to mix the micrograin-containing solution supplied from the micrograin-containing solution source and the diluted solution supplied from the diluted solution source and adjust density of the micrograin within the micro grain-containing solution; and a detector which is configured to detect a cavitation amount caused in the living tissue during treatment, and wherein the density adjuster is configured to adjust the density of the micrograins in the micrograin-containing solution source, depending on the cavitation amount detected by the detector.

2. The medical apparatus according to claim 1, wherein the density adjuster includes:
   a container which stores the micrograin-containing solution supplied from the micrograin-containing solution source and the diluted solution supplied from the diluted solution source;
   an agitation device which agitate the micrograin-containing solution and the diluted solution into the container.

3. The medical apparatus according to claim 1, wherein the micrograin feeder is configured to supply the micrograin-containing solution between the ultrasonic treatment portion and the living tissue before the ultrasonic vibration source is activated.

4. The medical apparatus according to claim 1, wherein a maximum grain size of the micrograins is 20 μm.

5. The medical apparatus according to claim 1, wherein a mass of each micrograins has 6 ng or less.

6. The medical apparatus according to claim 1,
   wherein the micrograins include at least one kind of grains among alumina-based grains, silica-based grains, titanium-based grains, magnesium-based grains, barium-based grains, and diamond-based grains.

7. The medical apparatus according to claim 1, comprising a liquid guide portion including a needle part which is configured to guide the micrograins-containing solution into the living tissue.

8. The medical apparatus according to claim 1, wherein the ultrasonic treatment portion further comprises
   a tip provided at the distal end of the ultrasonic treatment portion, and ultrasonic vibration is transmitted thereto,
   a guide portion which is configured to guide the tip to the living tissue as a treatment target, and
   a liquid feeder which is provided at the tip and is configured to supply the micrograin-containing solution supplied from the micrograin feeder to the living tissue as the treatment target.

9. The medical apparatus according to claim 8, wherein the tip includes a guide-portion insertion hole to allow the guide portion to be inserted and pulled out.

10. The medical apparatus according to claim 1, further comprising a calculus grasping portion which is apposed with the ultrasonic treatment portion and is configured to hold calculus.

11. The medical apparatus according to claim 10, wherein the calculus grasping portion is formed of a wire in a basket shape.

12. The medical apparatus according to claim 1, wherein whole micrograins within the micro grain-containing solution has a grain size equal to or smaller than an amplitude of the ultrasonic vibration.

13. The medical apparatus according to claim 1, wherein the diluted solution stored into the diluted solution source is normal saline solution.

* * * * *